US011407632B2

United States Patent
Mazzola et al.

(10) Patent No.: US 11,407,632 B2
(45) Date of Patent: Aug. 9, 2022

(54) PACKAGE DESIGN FOR DOSING SYSTEMS AND METHODS OF MANUFACTURE THEREOF

(71) Applicants: Dow Global Technologies LLC, Midland, MI (US); ModenaPak Industria Importação Exportação de Máquinas Automáticas Ltda., Santo André SP (BR)

(72) Inventors: Nicolas Cardoso Mazzola, Jundiai (BR); Eduardo Baldini, Sao Paulo (BR); Marcus-Vinicius Trombim Kerekes, Sao Paulo (BR); Bruno Rufato Pereira, Houston, TX (US); Harpreet Singh, Pearland, TX (US); Jeffrey E. Bonekamp, Midland, MI (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 17/256,244

(22) PCT Filed: Jun. 28, 2019

(86) PCT No.: PCT/US2019/039815
§ 371 (c)(1),
(2) Date: Dec. 28, 2020

(87) PCT Pub. No.: WO2020/006403
PCT Pub. Date: Jan. 2, 2020

(65) Prior Publication Data
US 2021/0229975 A1    Jul. 29, 2021

Related U.S. Application Data

(60) Provisional application No. 62/691,802, filed on Jun. 29, 2018.

(51) Int. Cl.
B67D 7/02 (2010.01)
B67D 7/20 (2010.01)
(Continued)

(52) U.S. Cl.
CPC ............. B67D 7/0216 (2013.01); B67D 7/20 (2013.01); F04B 43/0027 (2013.01);
(Continued)

(58) Field of Classification Search
CPC ....... B67D 7/0216; B67D 7/20; F04B 3/0027; F04B 3/1261; A47K 5/1208
(Continued)

(56) References Cited

U.S. PATENT DOCUMENTS 3,822,948 A    7/1974 Handl
5,105,992 A    4/1992 Fender et al.
(Continued)

FOREIGN PATENT DOCUMENTS

| EP | 1273800 A1 | 1/2003 |
| WO | 2017129193 A1 | 8/2017 |
| WO | 2018015618 A1 | 1/2018 |

OTHER PUBLICATIONS

International Search Report for International Application No. PCT/US2019/039815; International Filing date Jun. 28, 2019; Report dated Sep. 3, 2019; 5 pages.
(Continued)

*Primary Examiner* — Jeremy Carroll
(74) *Attorney, Agent, or Firm* — Cantor Colburn LLP

(57) ABSTRACT

Disclosed herein is a dispensable container comprising a container for a fluid; and a fitting for discharging the fluid from the container; wherein the dispensable container is monolithic and where the container and the fitting contact
(Continued)

each other seamlessly; and wherein the fitting comprises a conduit that has a higher aspect ratio than the container.

14 Claims, 4 Drawing Sheets

(51) Int. Cl.
  *F04B 43/00* (2006.01)
  *F04B 43/12* (2006.01)
  *A47K 5/12* (2006.01)
  *A47G 19/18* (2006.01)
(52) U.S. Cl.
  CPC ........ *F04B 43/1261* (2013.01); *A47G 19/183* (2013.01); *A47K 5/1208* (2013.01)
(58) Field of Classification Search
  USPC ........................................................ 222/206
  See application file for complete search history.

(56) References Cited

U.S. PATENT DOCUMENTS

| | | | | |
|---|---|---|---|---|
| 5,693,020 | A | | 12/1997 | Rauh |
| 6,003,733 | A | * | 12/1999 | Wheeler .............. B67D 1/0004 222/146.5 |
| 10,420,355 | B2 | * | 9/2019 | Vulpitta ................... A23G 9/28 |
| 10,894,705 | B2 | * | 1/2021 | Cocchi ................. B67D 1/0884 |
| 2007/0194045 | A1 | * | 8/2007 | Py ........................ B67D 1/0082 222/105 |
| 2012/0053520 | A1 | | 3/2012 | Kirkpatrick |
| 2013/0035444 | A1 | * | 2/2013 | Karjala ...................... C08J 5/18 525/180 |
| 2014/0352845 | A1 | | 12/2014 | Lev et al. |
| 2015/0129611 | A1 | * | 5/2015 | Vulpitta ............... B67D 3/0022 222/101 |
| 2015/0315005 | A1 | * | 11/2015 | Corbelli ............... B67D 1/0801 222/95 |
| 2016/0061199 | A1 | | 3/2016 | Hoefling |
| 2016/0317736 | A1 | | 11/2016 | Schabbach et al. |
| 2017/0015541 | A1 | * | 1/2017 | Vulpitta ............... B67D 1/0001 |
| 2017/0350388 | A1 | | 12/2017 | Quintarelli et al. |

OTHER PUBLICATIONS

Written Opinion for International Application No. PCT/US2019/039815; International Filing date Jun. 28, 2019; Report dated Sep. 3, 2019; 6 pages.

* cited by examiner

PACKAGE DESIGN FOR DOSING SYSTEMS AND METHODS OF MANUFACTURE THEREOF

CROSS REFERENCE TO RELATED APPLICATIONS

This application is a National Stage application of PCT/US2019/039815, filed Jun. 28, 2019, which claims the benefit of U.S. Provisional Application No. 62/691,802, filed Jun. 29, 2018, both of which are incorporated by reference in their entirety herein.

BACKGROUND

This disclosure relates to a package design for dosing systems and methods of manufacture thereof. In particular, this disclosure relates to package design for dosing systems that include a peristaltic pump.

Dosing systems generally use peristaltic pumps for discharging small and fairly constant dosages of a fluid to a user. Common applications include the discharge of foods, fluids such as toothpaste, liquid soap and tomato ketchup, small doses of medicine to patients, and the like.

FIG. 1 depicts an exemplary dosing system 100 that uses a peristaltic pump 200. The dosing system 100 comprises a dispensing container 102 (in which the fluid 104 to be discharged is stored) that is in communication with a fitting (e.g., a flexible hose) 106 through which a measured quantity of fluid is discharged. The fitting 106 is manufactured from a material that can be easily squeezed, such as, for example, an elastomer. The fitting 106 is generally attached to the container 102 via an attachment mechanism 103. In other words, the dispensing container 102 and the fitting 106 are two separate pieces that are attachable and detachable from one another. Disposed atop the container 102 is a lid 107 through which the dispensing container 102 is replenished with fluid.

The dispensing container 102 and the fitting 106 are generally mounted in dispensing equipment (not shown) that has a hand-operated or electronically operated dispenser 108. The dispenser 108 operates a peristaltic pump 200, which, upon activation permits one dose of fluid to be discharged from the disposable container 102 through the fitting 106.

The peristaltic pump 200 generally comprises a plurality of rotatable arms 112 each of which contact a wheel or roller 110A, 110B, 110C and 110D at their respective ends. Upon being rotated, the rollers 110A, 110B, 110C and 110D each contact the fitting 106 and squeeze it to force out a portion of the fluid contained within the fitting. As seen in the FIG. 1, the fluid present in the fitting between locations 114 and 116 is discharged during one quarter rotation of the arms 110C and 110D. The amount of fluid discharged per rotary motion of the arm is dependent upon the diameter of the fitting 106 as well as upon the number of arms and the length of the arm. As the fitting 106 returns to its original shape, it sucks additional liquid from a container (in order to compensate for the reduced pressure in the fitting) thus replenishing the volume of fluid present in the fitting.

While peristaltic pumps are finding more use in dosing systems because of their simple operating mechanism, dosing devices that use them suffer from a number of drawbacks, chief amongst them being that the dispensing container is expensive and/or uses a laborious cleaning processes.

When the container is to be replenished, a large vessel of fluid has to be transported from one dispensing station to another. The lid 107 is removed from the container 102 and fluid from the large vessel is used to replenish the container. This process is untidy with substantial amounts of fluid being spilled onto the dispenser as well as onto the floor. Depending upon the type of fluid being transferred (especially with food products), this process can result in contamination of the equipment.

The use of a two-piece dosing container—one piece being the dispensing container 102 and the other piece being the fitting 106, both of which are made of different materials and have different thicknesses produces problems related to efficiency. When the container 102 is to be inserted into dispensing equipment, it has first to be fitted with the fitting 106 and then placed in the dispensing equipment. This generally causes the fluid present in the container to flow out thus contaminating the container, the fitting and the dispensing equipment. The appearance of the equipment is also compromised.

It is desirable to have a container that can be removed when empty and replaced without the need for transporting a large reservoir of fluid to each dispenser location to refill the container. It is therefore desirable to have a container that does not require attachment and detachment of the fitting prior to use in the dispensing equipment to avoid the appearance of untidiness.

SUMMARY

Disclosed herein is a dispensable container comprising a container for a fluid; and a fitting for discharging the fluid from the container; wherein the dispensable container is monolithic and where the container and the fitting contact each other seamlessly; and wherein the fitting comprises a conduit that has a higher aspect ratio than the container.

Disclosed herein too is a dispenser comprising a cavity in operational communication with a passage; a peristaltic pump; and a dispensable container comprising a container that contains a fluid that is to be discharged; and a fitting for discharging the fluid from the container; wherein the dispensable container is monolithic and where the container and the fitting contact each other seamlessly; wherein the fitting comprises a conduit that has a higher aspect ratio than the container; where the container is disposed in the cavity and where the fitting is disposed in the passage; and wherein an arm of the peristaltic pump contacts the fitting via a roller to discharge a dose of fluid upon rotation of the arm.

Disclosed herein is a method of operating a dispenser comprising opening a swiveling block of the dispenser; where the dispenser comprises a cavity in operational communication with a passage; and a peristaltic pump; disposing a fluid filled dispensable container that comprising a) a container that contains a fluid that is to be discharged and b) a fitting for discharging the fluid from the container; where the dispensable container is monolithic and where the container and the fitting contact each other seamlessly; where the fitting comprises a conduit that has a higher aspect ratio than the container; where the container is located in the cavity and where the fitting is located in the passage; closing the swiveling block of the dispenser; operating the peristaltic pump to discharge the fluid present in the dispensable container; removing an empty dispensable container from the dispenser; and replacing the empty dispensable container with another fluid filled dispensable container.

DETAILED DESCRIPTION

Disclosed herein is a single-piece, single-use dispensing container (hereinafter "dispensing container") that may be used in a peristaltic pump-containing dispenser (hereinafter "dispenser"). The dispensing container comprises a container (for holding a fluid that is to be dispensed) and a fitting (through which the fluid is dispensed) that is manufactured in a single piece (i.e., it is monolithic—it is indivisible and cannot be taken apart without damaging it).

The dispensing container filled with fluid is placed in the dispenser. The peristaltic pump facilitates discharging a fairly constant dose of fluid each time it is activated. When the dispensing container if empty it can be removed from the dispenser and replaced with another filled dispensing container. The old used dispensing container can be thrown away.

Figure 1:
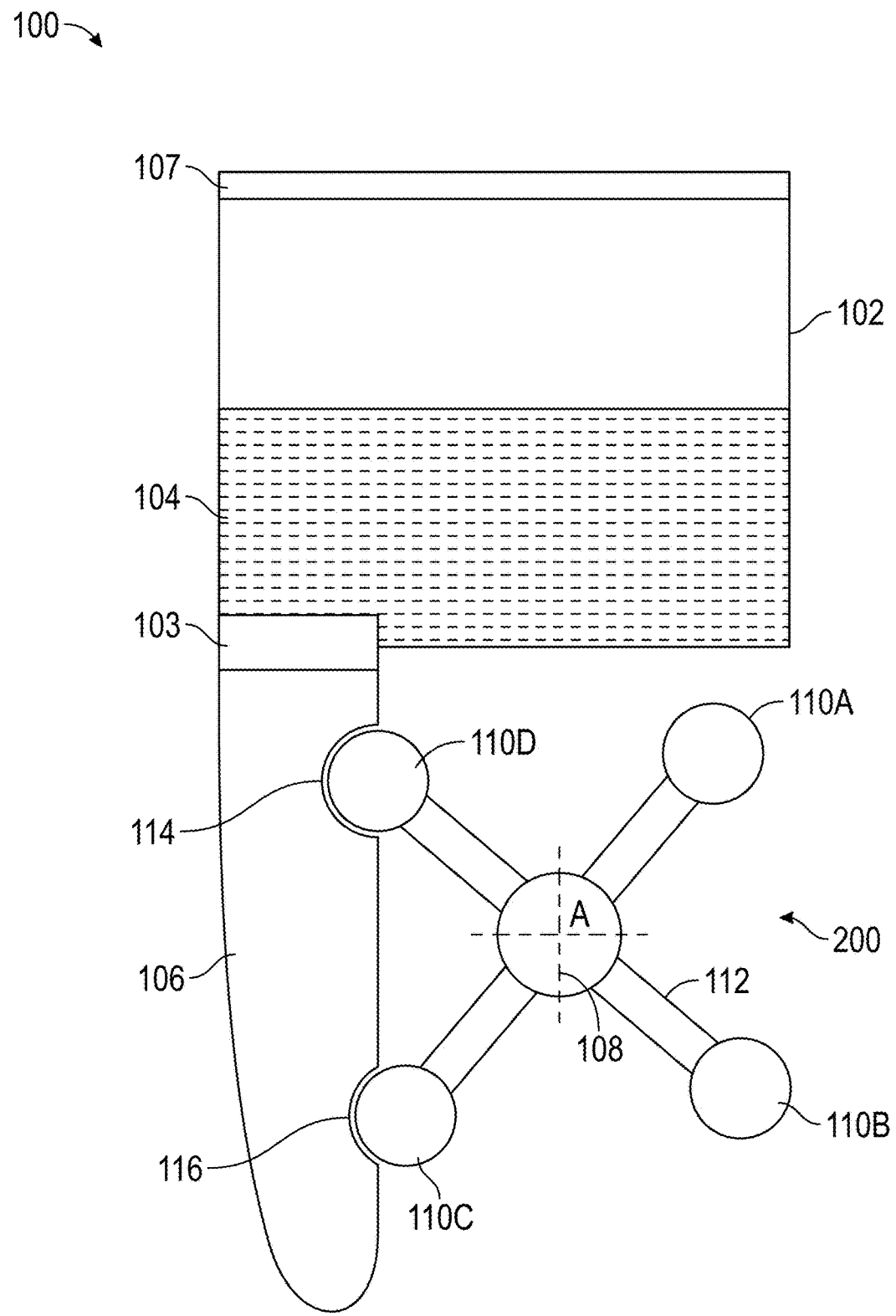
FIG. 1 is a schematic depiction of a prior art dispensing container and a peristaltic pump.
Figure 2B:
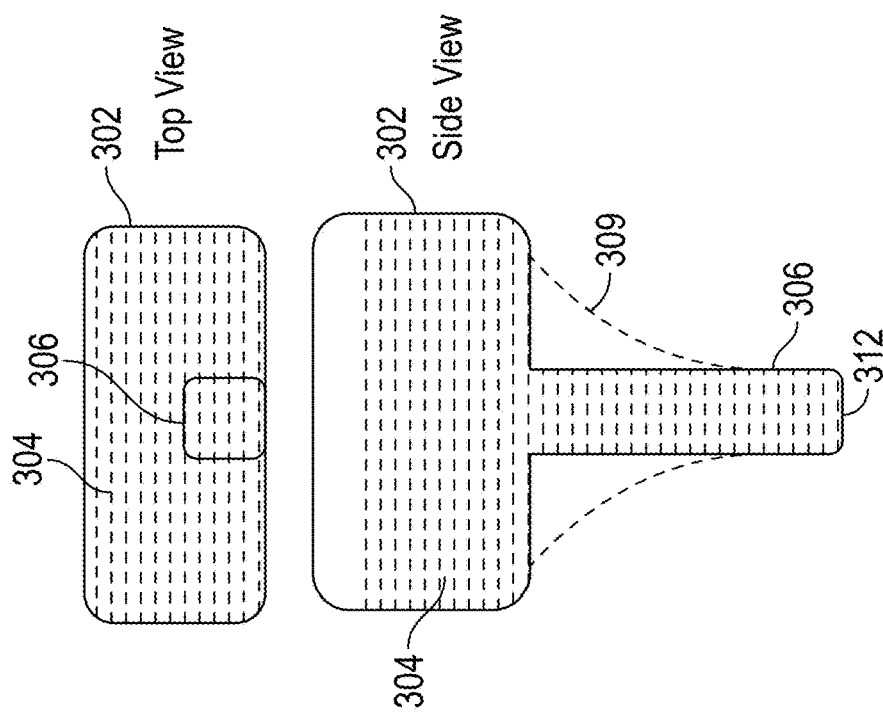
FIG. 2B depicts another side view along with the corresponding top view of the same dispensing container of the FIG. 2A.
Figure 2A:
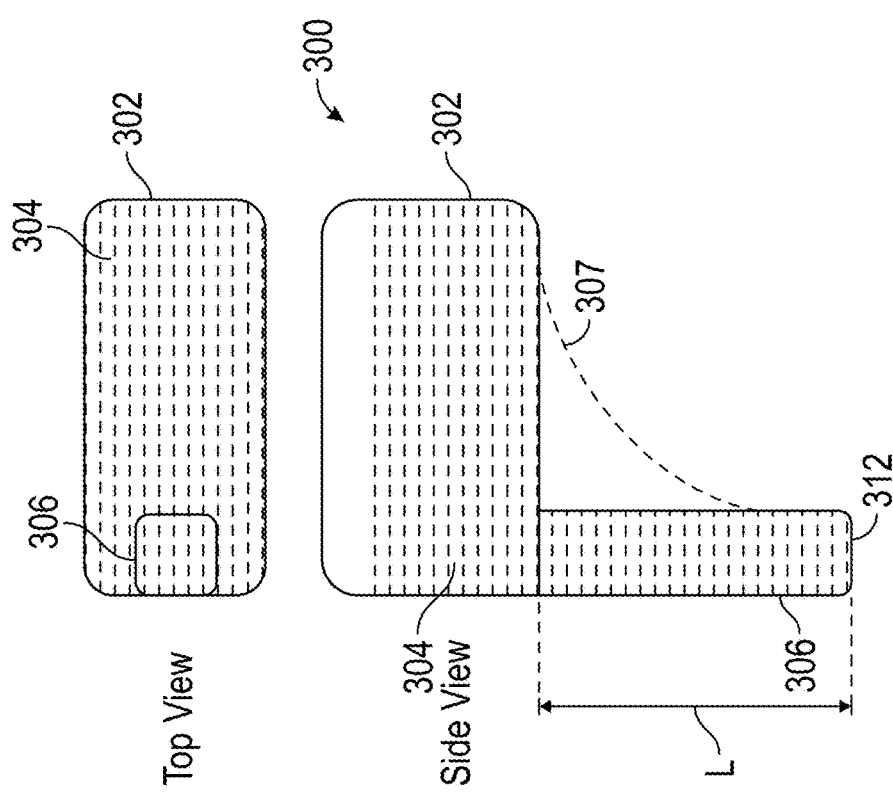
FIG. 2A depicts one side view and a corresponding top view of the dispensing container.

FIGS. 2A and 2B depict a single-piece dispensing container 300 that comprises a container 302 with a fitting 306. The FIG. 2A depicts one side view and a corresponding top view of the dispensing container 300, while the FIG. 2B depicts another side view along with the corresponding top view of the same dispensing container 300. Fluid 304 is stored in the container 302. The fitting 306 permits fluid contained in the container 302 to be discharged through it upon being pumped out by the peristaltic pump. The container 302 encloses a larger volume of fluid than the fitting 306.

While the top view in the FIGS. 2A and 2B show that the container and the fitting both have a rectangular cross-sectional area, the cross-sectional area of the container and the fitting may be independent of each other and may be circular, triangular, square, polygonal, or the like.

It is also to be noted that while the FIGS. 2A and 2B depict that the fitting extends perpendicular to the container and has a constant cross-sectional area along its length L, the cross-sectional area may be gradually varied (or gradually reduced) from the point that it contacts the container to the discharge point as depicted by dotted line 307 (see FIG. 2A) or dotted lines 309 (see FIG. 2B).

The fitting 306 is manufactured from the same material as the container 302 and seamlessly contacts the container 302. The fitting 306 has an aspect ratio that is greater than 2, preferably greater than 3 and more preferably greater than 5. In an embodiment, the fitting 306 is a conduit that serves to transfer fluid contained in the container 302 to a receiving vessel disposed below the outlet port 312 of the fitting 306. In an embodiment, depicted and detailed later in the FIGS. 3A and 3B, the fitting 306 may have disposed in it an elongated tube that facilitates the transfer of fluid from the container 302 to the outlet port 312. The receiving vessel may be located below the fitting 306 (i.e., the fluid is discharged into the receiving vessel) via gravity. Alternatively, the receiving vessel (or receiving container) may be in contact with the fitting via an attachment feature (e.g., screws, nuts, or the like).

In an embodiment, the fitting 306 is provided with an "easy open" feature wherein the seal brakes open with the pressure generated by the initial pump rotation. This easy open feature can include perforations (or the like) that can facilitate breaking of the seal with the application of pressure by the rollers of the peristaltic pump.

The container 302 is preferably manufactured from a polymeric film. The polymeric film may contain a single layer or may be multilayered. It is desirable for the polymeric film to be transparent so that the user can observe the level of fluid in the container.

The polymeric film may have an optical transparency that ranges from 30% to 100%, preferably 40% to 90% and more preferably 50 to 80% as measured using ASTM D 1746.

The container is preferably a flexible container that can be deformed using ordinary human force of less than 600 Newtons, preferably 10 to 500 Newtons, and more preferably 20 to 400 Newtons.

The fitting 306 and the container 302 have walls that are manufactured from the same polymeric material and contact each other without any seam therebetween. By using a container and fitting that are manufactured from a flexible material, they can be easily compressed by ambient atmospheric forces thus allowing for the discharge of their contents to a user. The volume of the discharge does not change with time so long as the container 302 encloses a volume that is greater than or equal to the amount discharged per rotation of the peristaltic pump. This design of the dispensing container 300 also facilitates an easy installation and replacement of the dispensing container 300 in the dispenser. The dispenser design is detailed later.

Organic polymers that are used in the walls of the dispensing container 300 may be selected from a wide variety of thermoplastic polymers, blend of thermoplastic polymers, thermosetting polymers, or blends of thermoplastic polymers with thermosetting polymers. The organic polymer may also be a blend of polymers, copolymers, terpolymers, or combinations comprising at least one of the foregoing organic polymers. The organic polymer can also be an oligomer, a homopolymer, a copolymer, a block copolymer, an alternating block copolymer, a random polymer, a random copolymer, a random block copolymer, a graft copolymer, a star block copolymer, a dendrimer, an ionomer, or the like, or a combination thereof. The organic polymers have number average molecular weights greater than 10,000 grams per mole, preferably greater than 20,000 g/mole and more preferably greater than 50,000 g/mole.

Examples of thermoplastic polymers that can be used in the dispensing container 300 include polyacetals, poly acrylics, polycarbonates, polyalkyds, polystyrenes, polyolefins, polyesters, polyamides, polyaramids, polyamideimides, polyarylates, polyurethanes, epoxies, phenolics, silicones, polyarylsulfones, polyethersulfones, polyphenylene sulfides, polysulfones, polyimides, polyetherimides, polytetrafluoroethylenes, polyetherketones, polyether ether ketones, polyether ketone ketones, polybenzoxazoles, polyoxadiazoles, polybenzothiazinophenothiazines, polybenzothiazoles, polypyrazinoquinoxalines, polypyromellitimides, polyquinoxalines, polybenzimidazoles, polyoxindoles, polyoxoisoindolines, polydioxoisoindolines, polytriazines, polypyridazines, polypiperazines, polypyridines, polypiperidines, polytriazoles, polypyrazoles, polycarboranes, polyoxabicyclononanes, polydibenzofurans, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, polypropylenes, polyethylenes, polyethylene terephthalates, polyvinylidene fluorides, polysiloxanes, or the like, or a combination thereof.

An exemplary thermoplastic polymer is a polyolefin. Exemplary polyolefins include polyethylene, polypropylene, copolymers of polyethylene, copolymers of polypropylene, and blends thereof.

Preferred polyolefin polymers include ethylene vinyl acetate copolymers (EVA), ethylene acrylic acid copolymers (EAA), ionomers, ethylene ethyl acrylate copolymers (EEA), ethylene butyl acrylate copolymers (EBA) low density polyethylene (LDPE), ultra-low density polyethylene (ULDPE), very low density polyethylene (VLDPE), linear low density polyethylene (LLDPE), medium density polyethylene (MDPE), high density polyethylene (HDPE), homopolymer polypropylene (hPP), polypropylene random copolymers (RCP), and polypropylene impact copolymers (ICP), olefin block copolymers (OBC's), propylene-based elastomers or plastomers (PBPEs). In some embodiments it is preferred that the polyolefin polymer has a melting point of at least 110° C., more preferably in the range of from 115° C. to 170° C.

Examples of thermosetting polymers include epoxy polymers, unsaturated polyester polymers, polyimide polymers, bismaleimide polymers, bismaleimide triazine polymers, cyanate ester polymers, vinyl polymers, benzoxazine polymers, benzocyclobutene polymers, acrylics, alkyds, phenol-formaldehyde polymers, novolacs, resoles, melamine-formaldehyde polymers, urea-formaldehyde polymers, hydroxymethylfurans, isocyanates, diallyl phthalate, triallyl cyanurate, triallyl isocyanurate, unsaturated polyesterimides, or the like, or a combination thereof.

Examples of thermoplastic polymeric blends include ethylene-propylene diene monomer, low density polyethylene/polyvinylidene chloride, acrylonitrile-butadiene-styrene/nylon, polycarbonate/acrylonitrile-butadiene-styrene, acrylonitrile butadiene styrene/polyvinyl chloride, polyphenylene ether/polystyrene, polyphenylene ether/nylon, polysulfone/acrylonitrile-butadiene-styrene, polycarbonate/thermoplastic urethane, polycarbonate/polyethylene terephthalate, polycarbonate/polybutylene terephthalate, thermoplastic elastomer alloys, nylon/elastomers, polyester/elastomers, polyethylene terephthalate/polybutylene terephthalate, acetal/elastomer, styrene-maleic anhydride/acrylonitrile-butadiene-styrene, polyether etherketone/polyethersulfone, polyether etherketone/polyetherimide polyethylene/nylon, polyethylene/polyacetal, or the like.

In an embodiment, the film used in the dispensing container 300 may be a multilayer film, where one of the layers is a barrier layer that reduces or eliminates the diffusion of water vapor and/or oxygen into it. The multilayer film may comprise 2 to 30 layers. The barrier layer may comprise polyamide (nylon 6, nylon 6, 6, or the like) polyvinylchloride, high density polyethylene (HDPE), or a combination thereof. The barrier layer may comprise a filler. Suitable fillers include clays, calcium carbonate, kaolin, mica, talc, feldspar, perlite, diatomaceous earth, silica gels, activated carbons, or the like, or combinations thereof.

The fluid carried by the dispensing container 300 may have a viscosity of 1 to 200,000 centipoise. Examples of fluids include tomato sauce, tomato ketchup, creams, creamers, beverages, toothpaste, soaps, antibacterial detergents, degreasers, cleansers, cosmetics, shampoos, medicines, ice cream, yogurt, or the like.

Figure 3B:
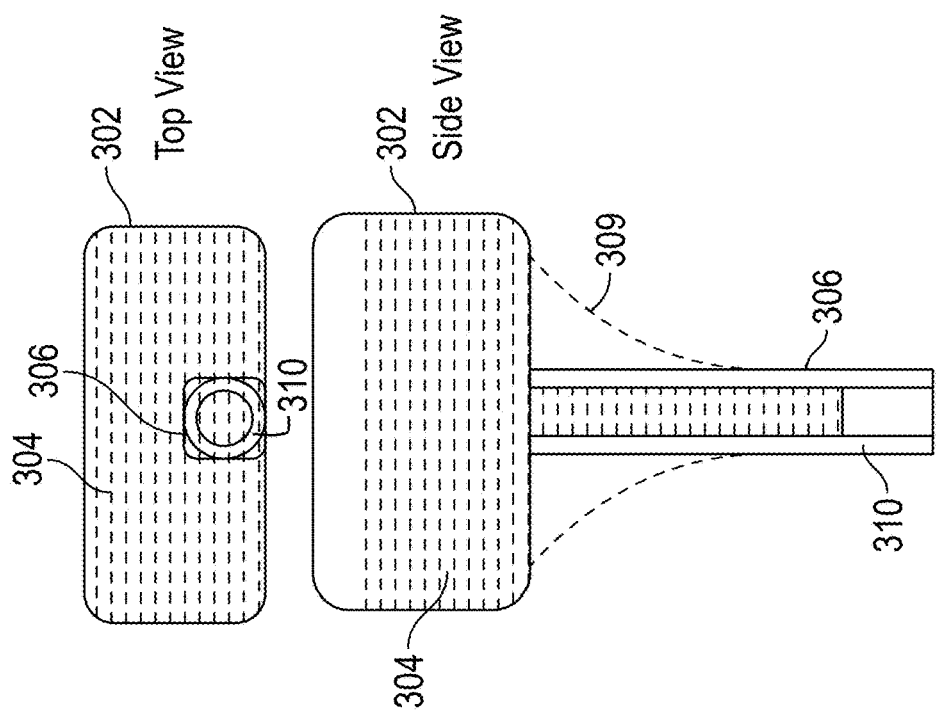
FIG. 3B depicts another side view and a corresponding top view of the dispensing container of the FIG. 3A with a flexible hose attached thereto.
Figure 3A:
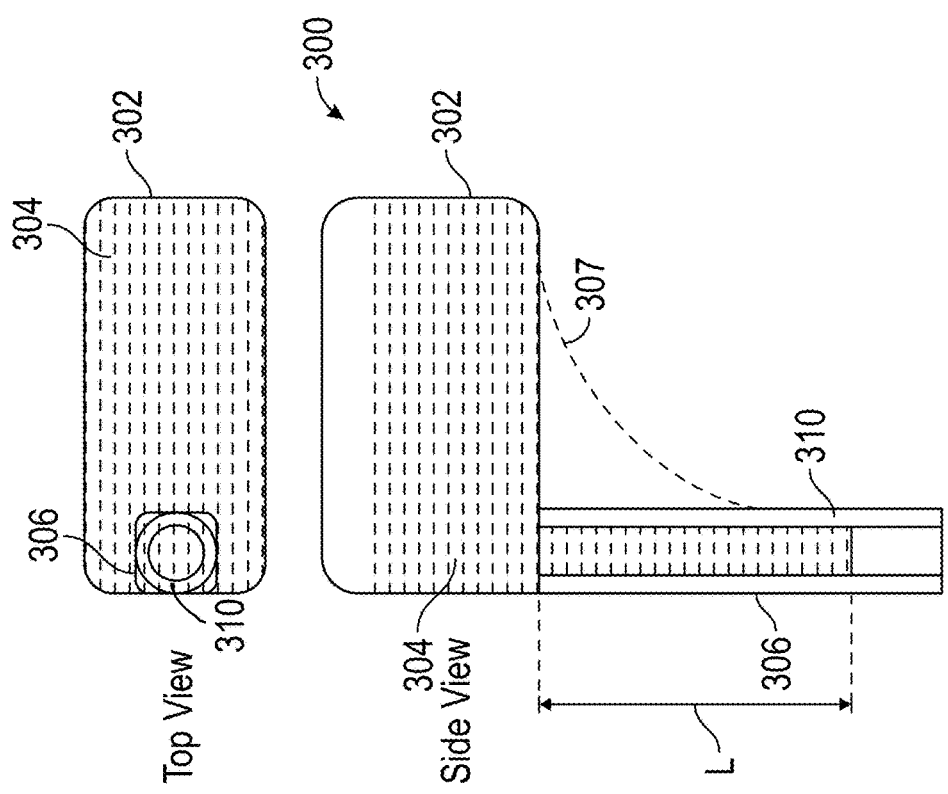
FIG. 3A depicts one side view and a corresponding top view of the dispensing container with a flexible hose attached thereto.

In an embodiment, the fitting 306 depicted in the FIGS. 2A and 2B may be fitted with a hose. This is depicted in the FIGS. 3A and 3B. The FIGS. 3A and 3B depicts two side views of the dispensing container 300 with a hose 310 attached to the fitting 306. In an embodiment, the hose is detachable and preferably manufactured from an elastomer. In another embodiment, the hose is permanently affixed to the fitting 306. The hose 310 is greater in length than the fitting 306 and protrudes beyond the fitting 306. In another embodiment, the hose 310 may be provided with a puncturing feature that can be used to puncture the fitting so that fluid can be transported from the dispensing container to the outside when activated by the peristaltic pump.

Examples of elastomers include polybutadienes, polyisoprenes, styrene-butadiene rubber, poly(styrene)-block-poly(butadiene), poly(acrylonitrile)-block-poly(styrene)-block-poly(butadiene) (ABS), polychloroprenes, epichlorohydrin rubber, polyacrylic rubber, silicone elastomers (polysiloxanes), fluorosilicone elastomers, fluoroelastomers, perfluoroelastomers, polyether block amides (PEBA), chlorosulfonated polyethylene, ethylene propylene diene rubber (EPR), ethylene-vinyl acetate elastomers, or the like, or a combination thereof.

The dispensing container 300 may be manufactured using blow molding, vacuum forming, 2-dimension formats (like sachets), or the like. In an embodiment, when the dispensing container 300 comprises a multilayered film, the film may first be co-extruded and then subjected to blow molding, vacuum forming or pouch-making. The dispensing container 300 thus manufactured may be filled with the desired fluid before sealing it and transporting it to vendors for use.

Figure 4:
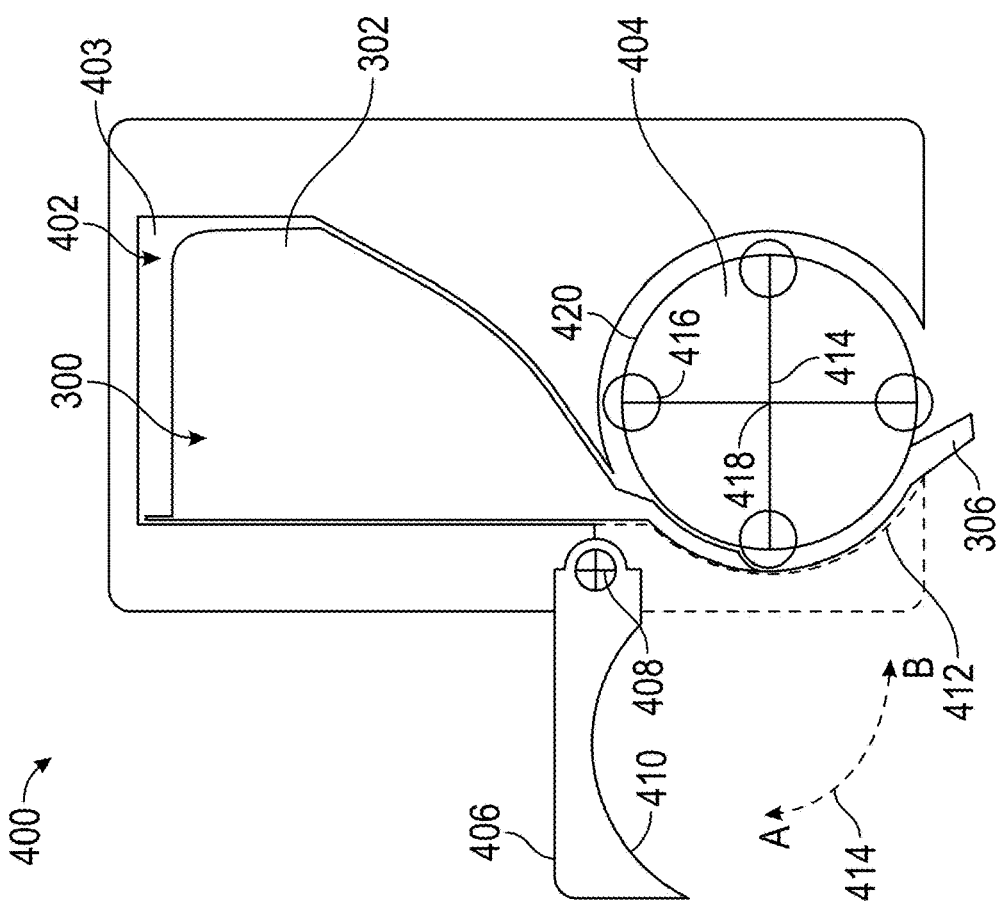
FIG. 4 depicts one exemplary embodiment of the internal parts of the dispenser.

The dispensing container 300 is used in a peristaltic pump-containing dispenser (the dispenser). FIG. 4 depicts one exemplary embodiment of the dispenser 400. The dispenser 400 comprises a cavity 402 that has a shape and size effective to accommodate the dispensing container 300. The cavity 402 comprises a large opening 403 and a narrow passage 412 disposed at an outlet end of the larger opening 403. The large opening 403 is in fluid communication with the narrow passage 412 and has a larger cross-sectional area than the narrow passage 412. The large opening 403 is sized to accommodate the container 302, while the narrow passage 412 accommodates the fitting 306. In an embodiment, the dispenser 400 may be provided with a feature (not shown) for holding, clamping or supporting the weight of the dispensing container 300 while it is located in the dispenser 400.

A peristaltic pump 404 is disposed on one side of the cavity 402. The peristaltic pump 404 is disposed on the side of the cavity 402 that the fluid flows towards. The narrow passage 412 is bounded by the peristaltic pump 404 on one side and by a curved surface 410 of swiveling block 406 on the other. The swiveling block 406 rotatably pivots about a swiveling pin 408 and can be rotated back and forth along path 414 (depicted by a dotted line). When the swiveling block 406 is rotated outwards from B to A along path 414, the narrow passage 412 is opened to accommodate the dispensable container 300 in the cavity 402. Upon installing the dispensable container 300 in the cavity 402 with the fitting 306 disposed in the narrow passage 412, the swiveling block 406 is rotated in the direction from A to B to facilitate contact between the fitting 306 and the peristaltic pump 404.

When the dispensable container 300 is empty, the swiveling block 406 is rotated outwards about pin 408 from B to A, the old dispensable container 300 is removed and a new dispensable container 300 that is filled with fluid in installed. After installation of the new dispensable container 300 in the cavity 402, the swiveling block 406 is rotated into the position and the dispenser may once again be used to dispense fluid.

The peristaltic pump 412 comprises a plurality of arms 414 that are equidistantly spaced along the circumference of rotation from the nearest neighboring arms. The plurality of arms pivot about axis 418 and can be rotated manually or via a motor. The motor may be an electrical motor or a pneumatic motor. While the FIG. 4 shows 4 arms, the pump 412 can have 2 to 20 arms, preferably 3 to 15 arms, and more preferably 4 to 10 arms. The circumferential distance between the arms (i.e., the angle between the arms) determines the dosage. For a given circumference, if the angle between the arms is increased (i.e., there are fewer arms), the dosage is increased and vice-versa. In another embodiment, if the length of the arms is increased, the dosage can be increased and vice-versa.

Each arm has its end a roller 416 that rotates about an axis disposed on the circumferential line 420. While the figures depict a "roller", any suitable device that can exert a local pressure on the fitting can be used. All rollers are equidistantly spaced from the axis of rotation 418 of the arms. As the rollers 416 rotate about axes mounted on circumferential line 420, each roller pinches the fitting 306 that is disposed in the passage 412 and squeezes a dose of fluid. The dose of fluid in the fitting is replaced with a new volume of fluid that flows from the container 302 to the fitting 306. Fluid replacement takes place by gravity and/or elastic recovery of dispensing fitting.

Figure 5:
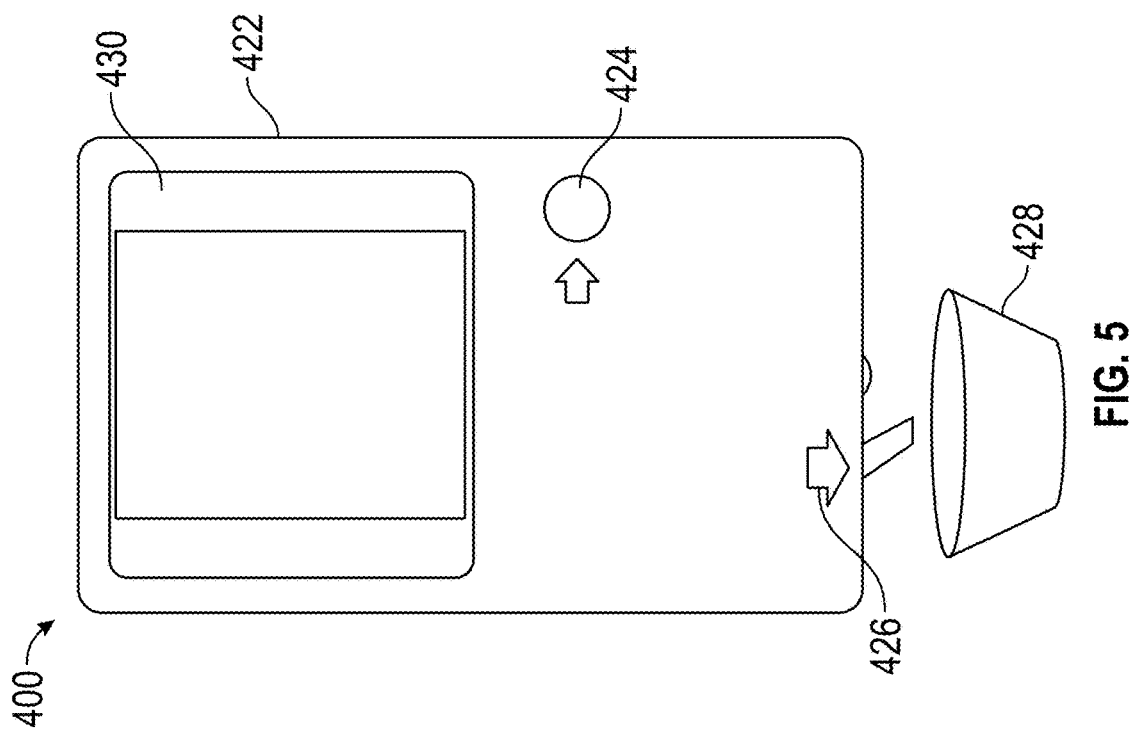
FIG. 5 depicts another exemplary embodiment of the dispenser with a cover disposed thereon.

FIG. 5 depicts another exemplary embodiment of the dispenser 400, with a cover 422 disposed on the dispenser 400. The cover 422 protects the mechanisms (i.e., the dispensing container 300, the peristaltic pump 404, mechanisms for activating the peristaltic pump (not detailed here) and the swiveling block 406) present in the dispenser 400 from unnecessary interference. The cover 422 may also be designed to be aesthetically appealing to the users of the device. As seen in the FIG. 5, the cover 422 has a port 424 for a switch that can be used to activate the peristaltic pump (if it is operated by an electrical motor or a pneumatic motor). Alternatively, if the peristaltic pump is hand-activated, it may be operated by a button or lever that would be visible to the user outside the cover 422.

The cover 422 may also contain directions/instructions to the user on how to use the dispenser 400. One instruction 426 displayed in the FIG. 5, pertains to the location of the receiving vessel 428 (also called a receiving container 428) for collecting the fluid discharged from the dispenser 400. The cover 422 may be manufactured from an opaque material, but may comprise a transparent window 430 that enables the provider of the dispenser 400 to see if the dispensing container 300 needs to be replaced. The cover 422 is generally fitted onto the dispenser 400 via a "tight fit". The "fit" is the clearance between the two mating parts, and the size of this clearance determines whether the parts can move independently from each other. In a tight fit, the two mating parts (in this case, the dispenser 400 and the cover 422) can be assembled and dissembled by hand. If it is desired other forms of affixing, such as for example, screws, pins, or the like can be used. In an exemplary embodiment, a tight fit between the dispenser 400 and the cover 422 is preferred.

The dispenser 400 and the cover 422 can be manufactured from a metal, a ceramic or from a polymer. Polymers are preferred.

Examples of metals include iron, brass, copper, aluminum, nickel, tin, zinc, or the like, or alloys thereof. The metals are in their elemental form. Examples of ceramics include silica, alumina, zirconia, titania, or the like, or a combination thereof.

The polymers that can be used in the manufacture of the dispenser 400 and the cover 422 can include some of the rigid polymers listed above in this document. Rigid polymers may be those that have glass transition temperatures or melting temperatures significantly higher than room temperature. Rigid polymers can also be obtained by filling the polymers with a large amount of fillers. Some of the fillers listed above may be used. The filler may be present in the polymer in an amount of 2 to 50 weight percent (wt %), preferably 3 to 30 wt % based on a total weight of the polymer and the filler.

The dispenser 400 and its constituent parts such as the swiveling block 406 and the cover 422 may be manufactured via injection molding, compression molding, extrusion molding, blow molding, or the like. After the parts are manufactured, they are assembled. With reference now again to the FIGS. 4 and 5, during the assembly of the dispenser 400, the swiveling block 422 is opened (moved in the direction from B to A) and the container 300 is placed in position (in the cavity 402) with the fitting 306 being placed in the passage 412. The tip 312 of the fitting 306 may be cut off prior to installing the container 300 into the cavity 402. A portion of the fitting 306 may protrude from the bottom of the dispenser 400 to discharge fluid into the receiving container 428. The cover 422 may then be placed and pressed into position on the dispenser 400. The dispenser 400 may be mounted on a wall if desired or alternatively, placed on a counter in the horizontal position.

If fluid is desired, the button 424 is depressed. The depressing of the button 424 activates a mechanism that causes the arms of the peristaltic pump to rotate. The rollers 416 pinch the fitting 306 and squeeze out a volume of fluid (present in the fitting 306) proportional to the circumferential distance between two successive rollers. At the same time, an amount of fluid proportional to the amount discharged is forced from the container 302 (under ambient atmospheric pressure) into the fitting 306 to compensate for the vacuum created by the preceding discharge.

This method of discharging a measured dose of fluid is advantageous in that it does not necessitate the fixing of a hose into the container. It also does not involve transporting large amounts of fluid from one dispenser to another to replenish the container when it is empty. The ability to quickly replace one container with another as described herein reduces waste and contamination.

In an embodiment, a single dispenser might comprise two or more dispensing containers pumping similar or different ratios of different fluids per turn.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A dispensable container comprising:
   a container for a fluid; and
   a fitting for discharging the fluid from the container;
   wherein the dispensable container is monolithic and where the container and the fitting contact each other seamlessly; and wherein the fitting comprises a conduit that has a higher aspect ratio than the container; wherein the fitting is provided with a seal that breaks open with pressure provided by a roller of a peristaltic pump.

2. The dispensable container of claim 1, where a wall of the dispensable container comprises a flexible material that can be deformed at a force of 600 Newtons or less.

3. The dispensable container of claim 2, where the flexible material comprises a polymer.

4. The dispensable container of claim 2, where the flexible material comprises a multilayer film that comprises a polymer.

5. The dispensable container of claim 4, where the multilayer film comprises one barrier layer that acts as a barrier to water vapor transfer and/or to oxygen transfer.

6. The dispensable container of claim 1, further comprising a flexible hose that is disposed in the fitting and where the flexible hose comprises an elastomer.

7. A dispenser comprising:
   a cavity in operational communication with a passage;
   a peristaltic pump; and
   a dispensable container comprising:
   a container that contains a fluid that is to be discharged; and
   a fitting for discharging the fluid from the container; wherein the dispensable container is monolithic and where the container and the fitting contact each other seamlessly; wherein the fitting comprises a conduit that has a higher aspect ratio than the container; wherein the fitting is provided with a seal that breaks open with pressure provided by a roller of a peristaltic pump;
   where the container is disposed in the cavity and where the fitting is disposed in the passage; and wherein an arm of the peristaltic pump contacts the fitting via a roller to discharge a dose of fluid upon rotation of the arm.

8. The dispenser of claim 7, further comprising a swiveling block that is opened to insert the dispensable container into the dispenser.

9. The dispenser of claim 7, where the fitting protrudes from the bottom of the dispenser to discharge fluid into a receiving container.

10. The dispenser of claim 7, where the dispensable container comprises a multilayer film.

11. The dispenser of claim 7, further comprising a flexible hose is that is disposed in the fitting and where the flexible hose comprises an elastomer.

12. A method of operating a dispenser comprising:
    opening a swiveling block of the dispenser; where the dispenser comprises a cavity in operational communication with a passage; and
    a peristaltic pump;
    disposing a fluid filled dispensable container that comprising a) a container that contains a fluid that is to be discharged and b) a fitting for discharging the fluid from the container; where the dispensable container is monolithic and where the container and the fitting contact each other seamlessly; where the fitting comprises a conduit that has a higher aspect ratio than the container; wherein the fitting is provided with a seal that breaks open with pressure provided by a roller of a peristaltic pump; where the container is located in the cavity and where the fitting is located in the passage;
    closing the swiveling block of the dispenser;
    operating the peristaltic pump to discharge the fluid present in the dispensable container;
    removing an empty dispensable container from the dispenser; and
    replacing the empty dispensable container with another fluid filled dispensable container.

13. The method of claim 12, where the peristaltic pump is hand operated.

14. The method of claim 12, where the peristaltic pump is operated using an electrical motor or a pneumatic motor.

* * * * *